United States Patent [19]

Kanamaru et al.

[11] Patent Number: 5,032,248

[45] Date of Patent: Jul. 16, 1991

[54] GAS SENSOR FOR MEASURING AIR-FUEL RATIO AND METHOD OF MANUFACTURING THE GAS SENSOR

[75] Inventors: Masatoshi Kanamaru, Ibaraki; Takeshi Harada, Toride; Yoshiro Ibaraki, Tsukuba; Sadayasu Ueno, Katsuta; Norio Ichikawa, Mito, all of Japan

[73] Assignee: Hitachi, Ltd., Tokyo, Japan

[21] Appl. No.: 362,619

[22] Filed: Jun. 7, 1989

[30] Foreign Application Priority Data

Jun. 10, 1988 [JP]  Japan ................................. 63-141534
Sep. 14, 1988 [JP]  Japan ................................. 63-228722

[51] Int. Cl.$^5$ .......................................... G01N 27/407
[52] U.S. Cl. ............................ 204/429; 204/153.18;
204/425; 204/426; 264/61; 264/62; 419/1;
419/8; 419/9; 419/10; 419/19; 419/46;
427/123; 427/124; 427/125; 427/126.3
[58] Field of Search ............... 204/427, 428, 429, 424,
204/425, 426, 15, 153.18; 427/123, 124, 125,
126.3; 264/61, 62; 419/8, 9

[56] References Cited

U.S. PATENT DOCUMENTS

| | | |
|---|---|---|
| 3,978,006 | 8/1976 | Topp et al. ............... 204/429 X |
| 4,021,326 | 5/1977 | Pollner et al. .............. 204/429 |
| 4,121,988 | 10/1978 | Sano et al. ................ 204/429 |
| 4,164,462 | 8/1979 | Ichikawa et al. ............ 204/429 |
| 4,177,112 | 12/1979 | Suzuki et al. ............ 204/153.18 |
| 4,383,906 | 5/1983 | Sano et al. .............. 204/424 X |
| 4,402,820 | 9/1983 | Sano et al. ................ 204/425 |
| 4,626,337 | 12/1986 | Hotta et al. ............... 204/429 |

FOREIGN PATENT DOCUMENTS

| | | |
|---|---|---|
| 2619746 | 11/1977 | Fed. Rep. of Germany . |
| 3021745 | 12/1980 | Fed. Rep. of Germany . |
| 2662 | of 1983 | Japan . |
| 24855 | 2/1983 | Japan . |
| 45962 | 3/1986 | Japan . |

Primary Examiner—T. Tung
Attorney, Agent, or Firm—Antonelli, Terry, Stout & Kraus

[57] ABSTRACT

The invention relates to a gas sensor for measuring an air-fuel ratio of an air-fuel mixture of an internal combustion engine and to a method of manufacturing the gas sensor. The sensor of the invention comprises: a solid state electrolyte layer made of an oxygen ion conductive metal oxide; a first electrode of a porous thin film having the catalyst function which was coated on one surface of the solid state electrolyte layer; a second electrode of a porous thin film having the catalyst function which was coated on the other surface of the solid state electrolyte layer; an electrode shielding layer made of a sintered material of ultra fine particulates whose average grain diameter is 1 μm or less which covers the surface other than the region of a predetermined area of the second electrode; and a gas diffusion layer made of a porous electric insulative metal oxide which covers the region of the predetermined area of at least the second electrode.

29 Claims, 5 Drawing Sheets

GAS SENSOR FOR MEASURING AIR-FUEL RATIO AND METHOD OF MANUFACTURING THE GAS SENSOR

BACKGROUND OF THE INVENTION

The present invention relates to a sensor for measuring an air-fuel ratio and, more particularly, to a gas sensor for measuring an air-fuel ratio which is used to control a flow rate of a fuel of an internal combustion engine and is suitable to measure an air-fuel ratio of an air-fuel mixture of the internal combustion engine. In general, in a fuel control system for automobiles using an air-fuel ratio measuring gas sensor, by measuring a concentration of oxygen ($O_2$) or unburnt gas ($H_2$, CO) in the exhaust gas, information regarding the air-fuel ratio is obtained, the information is fed back to an apparatus to control a supply amount of a fuel, that is, a gasoline and an air amount, and a mixture ratio of the air and gasoline, i.e., an air-fuel ratio (A/F) is controlled.

An example of air-fuel ratio measuring gas sensors has been disclosed in co-pending patent application Ser. No. 250,238, now U.S. Pat. No. 4,915,814, which was filed to the U.S.A. on Sept. 28, 1988, by the inventors some of whom are the same as the inventors of the present patent application. The conventional gas sensor mentioned above has a wide air-fuel ratio measurable range from a rich region to a lean region of the air-fuel ratio.

For such a gas sensor to detect the wide air-fuel ratio range, in order to obtain the accurate air-fuel ratio information, the sensor must be manufactured by accurately managing the area (catalyst active region) of a reactive electrode of the sensor. The reasons will now be described with reference to the drawings.

Figure 1:
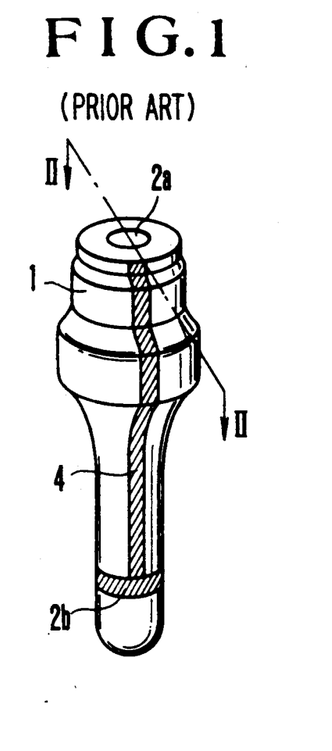
FIG. 1 is an external view of a gas sensor for measuring an air-fuel ratio.
Figure 2:
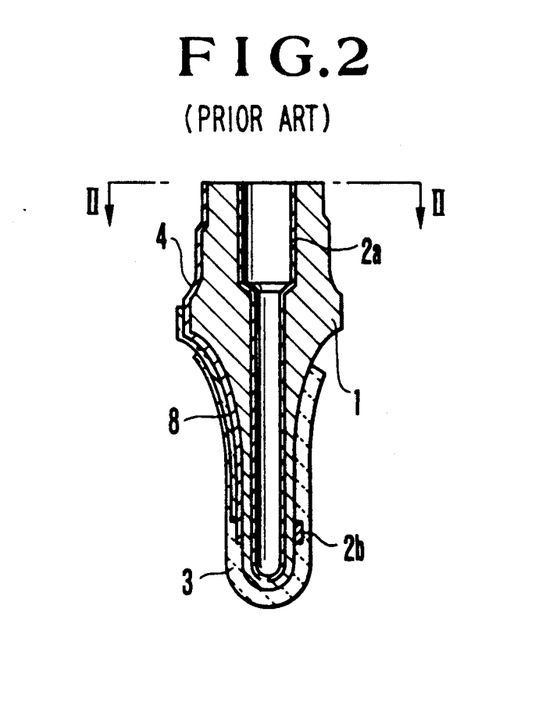
FIG. 2 is a cross sectional view taken along the line II—II in FIG. 1 showing the gas sensor.
Figure 3:
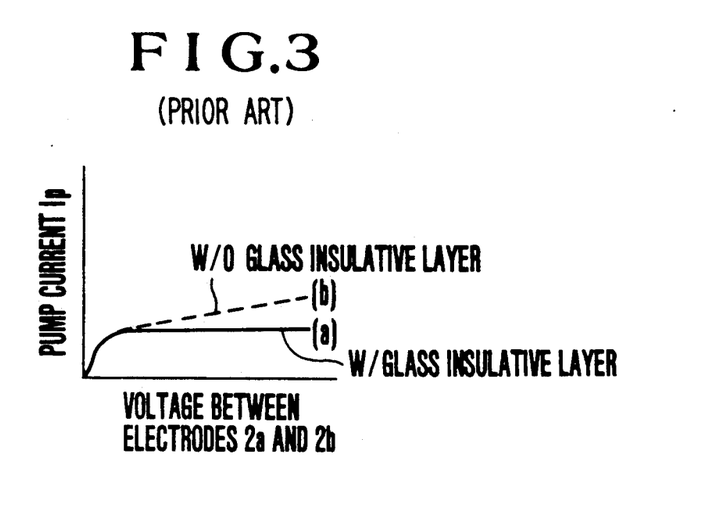
FIG. 3 is a voltage/current characteristic diagram of the sensor.

FIG. 1 is an external view showing an electrode position of a general gas sensor for measuring an air-fuel ratio. FIG. 2 is a vertical sectional view taken along the line II—II in FIG. 1 showing the air-fuel ratio measuring gas sensor of the limiting current type. FIG. 3 is a diagram showing electric characteristics in the cases where a glass insulative layer exists and where it does not exist.

In general, inside and outside reactive electrodes on a solid state electrolyte 1 of the gas sensor for measuring the air-fuel ratio are formed by plating platinum. As shown in FIG. 1, an outside reactive electrode 2b is formed like a ring. A stripe-shaped lead electrode 4 is connected to the reactive electrode 2. The reactive electrode 2b and lead electrode 4 are simultaneously formed by the platinum plating by masking the portions other than the electrode portions.

As shown in FIG. 2, an inside reactive electrode 2a is formed by plating platinum onto the whole surface of the inside of the solid state electrolyte 1. This is because it is very difficult to form the ring-shaped reactive electrode on the inside of the electrolyte 1 in a manner similar to the outside ring-shaped reactive electrode and to form the stripe-shaped lead electrode since the inner diameter of the inside of the electrolyte 1 is small. Therefore, the inside reactive electrode 2a is formed so as to also function as the inside lead electrode by plating platinum to the whole surface of the inside.

The principle of the air-fuel ratio measuring gas sensor will now be described with reference to FIGS. 2 to 4.

The oxygen gas existing on the exhaust gas side passes through a gas diffusion layer 3 and is ionized by the outside reactive electrode 2b due to the catalyst reaction. The oxygen ions $O^{2-}$ pass through the solid state electrolyte 1 and move to the atmosphere side. At this time, an amount of oxygen gas which passes is restricted by the gas diffusion film 3 and exhibits a saturation characteristic as shown by (a) in FIG. 3.

Figure 4:
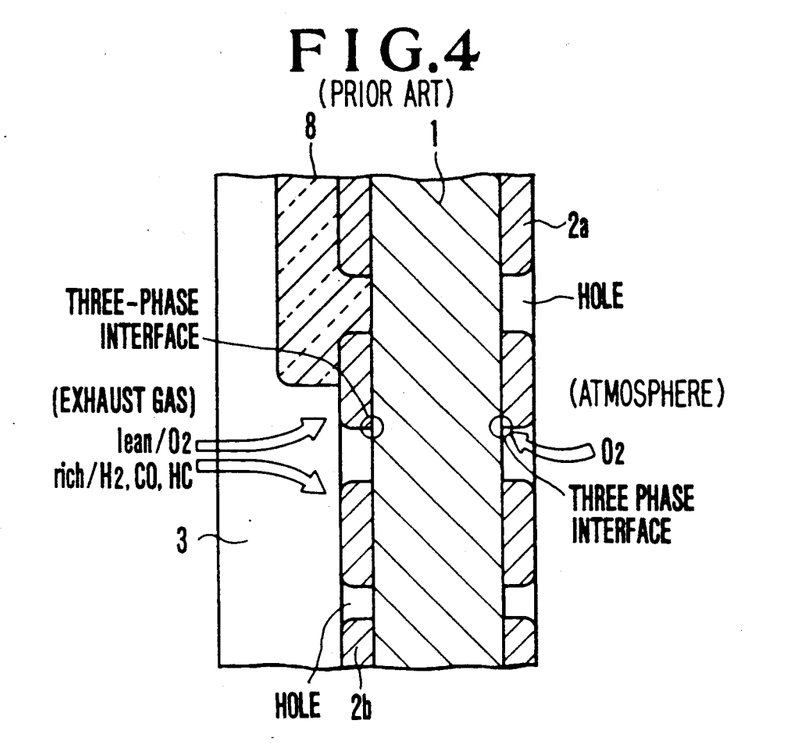
FIG. 4 is a partial enlarged diagram of a reactive region of the sensor.

FIG. 4 shows an enlarged diagram of the portion which contributes to the reaction of the sensor. When the air-fuel mixture is set to a value on the lean side, oxygen is dominant among the components in the exhaust gas. The oxygen molecules pass through the gas diffusion layer 3 and reach the reactive electrode 2b. The reactive electrode 2b is made of porous platinum and has a number of holes as shown in the diagram. In the hole portion, a three-phase interface in which platinum, solid state electrolyte 1, and gas molecules simultaneously exist is formed. The catalyst function occurs at the three-phase interface. According to the reaction at the three-phase interface when the air-fuel mixture is lean, the oxygen molecules which pass through the diffusion layer 3 react to the electrons which are provided from the electrode and the following reaction occurs.

$$O_2 + 4e^{2-} \rightarrow 2O^{2-}$$

The oxygen ions generated pass through the solid state electrolyte 1 having a potential gradient and reach the inside reactive electrode 2a, so that a pump current is caused.

When the air-fuel mixture is rich, the main components in the exhaust gas are hydrogen, carbon monoxide, and hydrocarbon. In this case, the oxygen molecules on the atmosphere side are ionized by the inside reactive electrode 2a and pass through the electrolyte 1 and reach the three-phase interface of the outside reactive electrode 2b. On the other hand, the molecules of $H_2$, CO, and HC in the exhaust gas pass through the gas diffusion layer 3 and reach the three-phase interface of the outside reactive electrode 2b and react to the oxygen ions as follows.

$$CO + O^{2-} \rightarrow CO_2 + 2e^-$$

$$H_2 + O^{2-} \rightarrow H_2O + 2e^-$$
$$2HC + 5O^{2-} \rightarrow 2CO_2 + H_2O + 10e^-$$

Thus, a pump current is caused. The direction of the current in this case is opposite to that in the case where the air-fuel mixture is lean.

In the portion where a glass insulative layer 8 covers the electrode 2b, the molecules or the molecules of hydrogen, carbon monoxide, and hydrocarbon cannot pass through the in of the glass, so that the catalyst function by the three-phase interface is not effected.

FIG. 3 shows a limiting value by a solid line in which the pump current constant. In FIG. 3, an axis of abscissa denotes a voltage V between electrodes and an axis of ordinate indicates a pump current $I_p$. When the air-fuel ratio A/F is changed, the limiting current value corresponding to the relevant air-fuel ratio is obtained.

The limiting current value is proportional to the area (effective area of the holes of the reactive electrode) of the reactive electrode. Therefore, to obtain the gas sensor having the output which accurately corresponds to the air-fuel ratio, the reactive electrodes must be formed by accurately managing the area of the outside reactive electrode 2b which faces the inside reactive electrode 2a through electrolyte 1.

However, the outside lead electrode 4 is formed by platinum having the same catalyst function as that of the outside reactive electrode 2b and also faces the inside reactive electrode 2a. Therefore, a pump current due to the oxygen ions also flows even in the portion where the lead electrode 4 faces the inside reactive electrode 2a. The value of the pump current in the lead electrode portion has a very large variation and gives a measurement error because the temperature distribution in the lead electrode portion by a heater in the sensor is not uniform. (The temperature is also one of the parameters which changes the pump current.)

Therefore, with respect to the outside lead electrode 4, the catalyst function thereof needs to be restricted so as not to contribute to the pump current, or the oxygen molecules or unburnt gas molecules ($H_2$, CO, HC) need to be blocked so as not to reach the lead electrode surface. The glass insulative layer 8 shown in FIG. 2 has such a function as to block the gas molecules.

In the case where the glass insulative layer 8 shown in FIG. 2 does not exist, the current characteristic of the sensor does not have a limiting current value as shown by a broken line in (b) in FIG. 3. This is because, as mentioned above, when the glass insulative layer 8 does not exist, the gas molecules are also ionized even on the lead electrode 4 by the catalyst reaction (In the lean region, the oxygen molecules emit the electrons and become the oxygen ions and pass through the solid state electrolyte 3 and reach the inside electrode 2a. In the rich region, the molecules of hydrogen, carbon monoxide, and hydrocarbon are ionized and are combined with the oxygen ions which passed through the electrolyte 3.) and a pump current flows and is added to the pump current which is caused due to the outside reactive electrode 2b.

Therefore, it is extremely important to prevent the ionization of the gas molecules at the lead electrode 4 and to prevent the gas molecules which propagate on the surface of the lead electrode and enter the reactive electrode 2b.

In JP-A-58-24855 which has been filed to Japanese Patent Office on Aug. 5, 1981, by Nippondenso Co., Ltd. and has been laid open on Feb. 14, 1983, there has been disclosed a construction such that after a lead electrode was covered by a coating film having a glass impermeability of a glass of a high melting point, a gas diffusion layer is formed by the plasma flame coating.

In JP-A-61-45962 which has been filed in the Japanese Patent Office on Aug. 9, 1984, by Toyota Central Research & Development Labs., Inc. and has been laid open on Mar. 6, 1986, there has been disclosed a construction in which an insulative layer is formed between a lead electrode and a solid state electrolyte.

In JP-A-58-2662(U) which has been filed in the Japanese Patent Office on June 29, 1981, by Nihon Denshi Kiki Kabushiki Kaisha, there has been disclosed a construction in which outside and inside lead electrodes of a solid state electrolyte are formed at different positions.

Like a technique disclosed in JP-A-58-24855, a glass having a high melting point is formed as a glass insulative layer onto the lead electrode of platinum. In the manufacturing processes, after a glass of a high melting point was coated onto the platinum lead electrode, it is sintered at about 600° C. by using an electric furnace or the like. Therefore, the adhesive property between platinum and glass of a high melting point is bad and their coefficients of thermal expansion largely differ. Thus, it is very difficult to form a thin film. On the contrary, it is considered that it is difficult to cover the whole surface of the lead electrode unless the film is formed thickly.

On the other hand, in the next step, to form the gas diffusion layer onto the glass insulative layer or the like, pulverulent magnesiaspinel is used as a material and the gas diffusion layer is formed by the plasma flame coating. In this case, magnesiaspinel having a melting point of about 2100° C. is supplied into the plasma jet and is semi-fused and is struck against the glass insulative layer at a high speed, thereby forming the gas diffusion layer. Thus, there is a problem such that the glass of a high melting point which is used for the glass insulative layer causes a crack by the influence when magnesiaspinel was struck against the glass at a high speed. Therefore, there occur problems of the ionization of the oxygen gas on the lead electrode which occurs due to the crack existing in the glass insulative layer and an erroneous current which is caused by the oxygen gas which enters from the upper portion of the lead electrode. Thus, there is a problem such that air-fuel ratio cannot be accurately detected.

On the other hand, even the technique disclosed in JP-A-61-45962 relates to the construction such that the glass insulative layer is formed by the plasma flame coating and also has a problem similar to that in the technique disclosed in JP-A-58-24855. The technique disclosed in JP-U-58-2662 has a problem such that the working step to form the inside and outside electrodes at deviated positions is complicated and the producing costs are high.

SUMMARY OF THE INVENTION

It is an object of the present invention to solve the problems of the foregoing techniques and to provide a gas sensor for measuring an air-fuel ratio having a high productivity and to provide a method of manufacturing such a sensor. According to a gas sensor of the present invention, in order to prevent the ionization of gas molecules at a lead electrode and to prevent that the gas molecules pass through the lead electrode and reach a reactive electrode, a glass insulative layer by the plasma flame coating is not used but there is provided a structure such as to lose the catalyst function of the lead electrode or to block the contact of the gas molecules with a three-phase interface. With such a structure, the erroneous measurement of the sensor due to the occurrence of cracks during the manufacturing is prevented, and a gas sensor for measuring an air-fuel ratio having a high quality and a high productivity is provided.

According to an embodiment of a structure of a practical sensor which accomplishes the above object, an ultra fine particulate layer whose average grain diameter is 1 μm or less is coated onto a lead electrode and is sintered. Thus, an alloy layer is formed by the lead electrode and an ultra fine particulate material and the catalyst function of the lead electrode is lost. Or, a dense thin film of the fused particulates is formed onto the lead electrode and the thin film blocks that gas molecules from reaching the three-phase interface of the lead electrode. According to another embodiment of the invention, the lead electrode surface is fused by a high density energy, for instance, plasma jet, laser, electron beam, or the like and the holes in the lead electrode are closed, thereby losing the three-phase interface.

According to an embodiment of a method of manufacturing the gas sensor for measuring an air-fuel ratio by the invention, the ultra fine particulate film is formed onto the lead electrode by a method such as plating, vacuum evaporation deposition, sputtering, or coating of a diffusion liquid. There is also a method whereby the lead electrode is formed on the solid state electrolyte before the electrolyte is sintered and, thereafter, the electrolyte is sintered and the lead electrode is fused, thereby closing the holes.

As an ultra fine particulate material of the invention, it is preferable to use a metal group which does not have the catalyst function such as titanium, tin, silicon, nickel, gold, or the like whose average grain diameter is 1 μm or less or to use ceramics such as zirconia.

BRIEF DESCRIPTION OF THE DRAWINGS

FIG. 10 (a-d) is a diagram showing another embodiment of a method of manufacturing the gas sensor of the invention.

DESCRIPTION OF THE PREFERRED EMBODIMENTS

Embodiments of the present invention will be described hereinbelow with reference to FIGS. 5 to 8.

First, an ultra fine particulate layer of a gas sensor for measuring an air-fuel ratio shown in FIG. 5 will be described. The gas sensor is used to control the air-fuel ratio of an air-fuel mixture.

Figure 5:
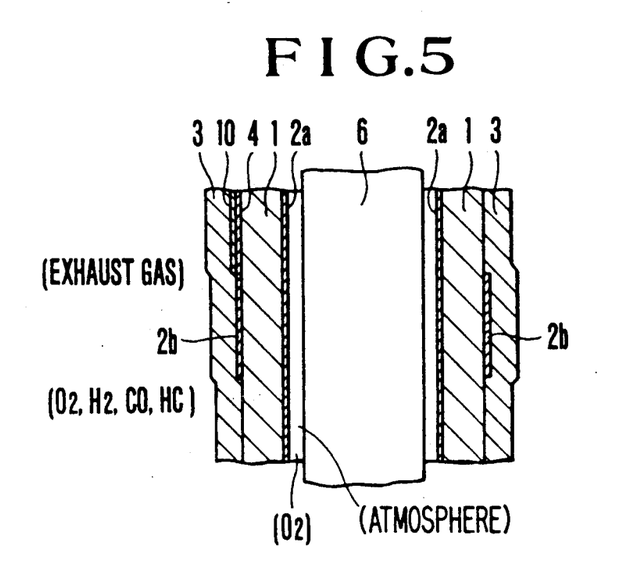
FIG. 5 is a partial cross sectional view of an embodiment of a gas sensor according to the present invention.

FIG. 5 is a cross sectional view of the portions around reactive electrode portions of the air-fuel ratio measuring gas sensor of the invention. Reference numeral 1 denotes the solid state electrolyte device (hereinafter, simply referred to as a solid state electrolyte) comprising a metal oxide which can propagate oxygen ions. In the embodiment, the solid state electrolyte 1 comprises zirconium oxide (zirconia) which is partially stabilized by solid dissolving yttrium oxide (yttria). Reference numeral 2 (general reference numeral of 2a and 2b) denotes the porous thin-film shaped reactive electrodes which are formed by plating platinum onto the inside and outside surfaces of the electrolyte 1. Since the outside reactive electrode 2b is an electrode to detect the oxygen gas, its area is accurately controlled by the masking when platinum is plated.

Reference numeral 3 denotes the gas diffusion layer comprising an electrical insulative metal oxide which is formed so as to cover the outside reactive electrode 2b; 4 indicates the lead electrode; and 6 represents a heater to heat the solid state electrolyte 1.

The lead electrode 4 connected to the outside reactive electrode 2b is formed by the platinum plating simultaneously with the reactive electrode 2b. To completely interrupt the reaction with the exhaust gas, the lead electrode 4 is covered by a thin film layer 10 of a sintered material of ultra fine particulates. In consideration of the point of the adhesive property between the lead electrode 4 and platinum, as a material of the ultra fine particulates, it is suitable to use a metal such as titanium (Ti), tin (Sn), silicon (Si), nickel (Ni), gold (Au), or the like having the excellent reactive performance to platinum. On the other hand, the gas diffusion layer 3 is formed on the outsides of them by the plasma flame coating. In general, magnesiaspinel is used as a material of the gas diffusion layer 3. As a method of forming the gas diffusion layer, it is not limited to the plasma flame coating but it is also possible to use a method whereby an electric insulative metal oxide of ultra fine particulates is diffused into a liquid and, thereafter, it is coated by using a method such as dipping method, brush painting method, spray method, spin coating method, blading method, or the like and is sintered, thereby forming the gas diffusion layer.

By coating the lead electrode 4 by the thin film layer 10 of the ultra fine particulate sintered material, platinum of the lead electrode 4 reacts to the ultra fine particulates, so that platinum and alloy are formed. Or, a thin film is formed at the interface of the lead electrode by the fusion of the ultra fine particulates. Thus, the lead electrode 4 is perfectly isolated from the exhaust gas. It is sufficient that the thin film is formed as a dense film such as not to pass the smallest hydrogen molecules among the gas components. Therefore, the gas diffusion layer 3 which is formed on the outsides of the lead electrode 4 and ultra fine particulate layer 10 does not always need to coat the whole region of the outside of the solid state electrolyte 1 but it is sufficient to coat the whole surface of at least the outside reactive electrode 2b.

An ultra particulate coating method in the embodiment of FIG. 5 will now be practically explained.

First, oxygen ion conductive metal oxide, for instance, the powder of zirconia is put into the die for the solid state electrolyte and is pressed to form a solid matter. Next, the solid state electrolyte is sintered at a high temperature. The portions other than the electrodes of the surface of the solid state electrolyte 1 formed by sintering are masked and platinum is plated, thereby forming the inside reactive electrode 2a, outside reactive electrode 2b, and lead electrode 4 in a lump.

Next, ethyl alcohol of 20 cc is mixed to nickel ultra fine particulates of 5 g whose average grain diameter is 0.1 μm or less (for instance, 0.04 μm). The nickel ultra fine particulates are diffused in the ethyl alcohol by an ultrasonic dispersing device. The resultant liquid is coated onto the lead electrode 4 by a method such as brush painting, spraying, or the like and is naturally dried. Thereafter, it is sintered for one hour at 950° C. under an argon atmosphere. A film having a thickness of about 30 μm was formed by the above steps.

In the case of adjusting a thickness of the thin film, a thinner film can be formed by changing the mixture ratio of the ultra fine particulates and ethyl alcohol. That is, when a dilution amount of alcohol is increased, the thin film is formed thinner. The thickness of the thin film relates to an electric resistance value of the lead electrode 4. The electric resistance value must be set to a predetermined value so as to obtain a desired output characteristic. On the other hand, to form the gas diffusion layer 3 in the next step, it is desirable that the thickness of the ultra fine particulate thin film on the lead electrode 4 is thin.

On the other hand, the sintering temperature can be freely set to a value in a wide range by changing the material of the ultra fine particulates. Thus, a method of coating the gas diffusion layer 3 which is executed in the next step can use a method of coating and sintering the gas diffusion layer by using a dipping process or the like other than the plasma flame coating as mentioned above. Hitherto, the glass of a high melting point has been used as a glass insulative layer. However, since the softening temperature of the glass of a high melting point is about 650° C., it is considered that in the case of forming the gas diffusion layer at temperature of 650° C. or higher, the glass of a high melting point cannot endure a thermal distortion or the like and cracks occur. However, according to the invention, since no glass insulative layer is used, by using the embodiment, it is possible to freely select the method of forming the gas diffusion layer 3 which is coated in the next step (the process can be performed at a temperature higher than the melting point of glass). On the other hand, since the thin film is formed thinner on the lead electrode 4 as compared with the glass of a high melting point, the gas diffusion layer can be also easily formed.

Further, in addition to the foregoing embodiment, an ultra fine particulate diffusion liquid such as sol, gel, or the like can be also used. Compound ultra fine particulates and ultra fine particulates of nitride or oxide can be solely used or can be also used as a mixture by mixing them at a proper ratio.

Figure 6:
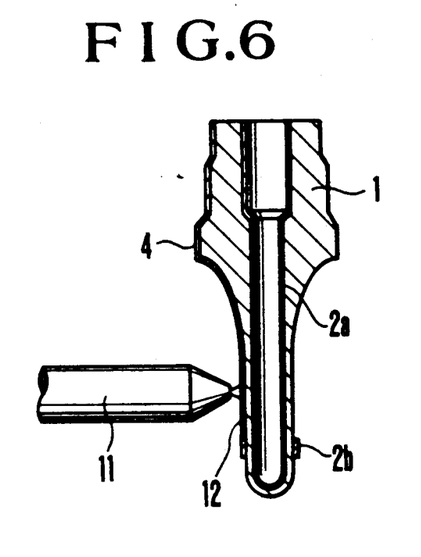
FIG. 6 is a diagram showing an embodiment of a method of manufacturing the gas sensor of the invention.

FIG. 6 shows an embodiment in which the lead electrode is thermally treated by using a high energy as a heat source. In the diagram, the same parts and components as those shown in FIG. 5 are designated by the same reference numerals and their descriptions are omitted.

As shown in FIG. 6, the portion on the lead electrode 4 formed by the platinum plating is thermally treated by using a plasma jet torch 11, so that the catalyst function can be lost for a thermally treated lead electrode portion 12.

In more detail, since the platinum lead electrode is formed like a porous thin film, by thermally treating the surface of the lead electrode by using an ultrahigh temperature plasma which is generated from a plasma jet torch, the porous portion is fused and filled with platinum, so that the three-phase interface is extinguished. Thus, the lead electrode loses the catalyst function to ionize the oxygen gas and only the conductivity exists. The similar effect can be also obtained by using a laser or an electron beam as a high density energy heat source.

Further practically speaking, the device (solid state electrolyte) after the platinum plating was completed is fixed by upwardly directing the lead electrode. The plasma jet torch is arranged over the device. In order to keep the distance between the device and the torch constant, they are moved by a profiling apparatus provided for that purpose. It is desirable that the conditions at this time are set such that a plasma current is 50 A and a moving speed is 0.2 mm/sec.

By using the above method, the catalyst function of the lead electrode can be lost in a short time and there is no need to form a glass insulative layer onto the lead electrode surface. Therefore, in the case of forming a gas diffusion film in the next step, there is no need to consider the influence by the glass insulative layer and an inconvenience such as an influence of an erroneous current or the like which is generated due to the cause of the glass insulative layer is also eliminated. Further, the productivity and heat resistance are also improved.

Figure 7:
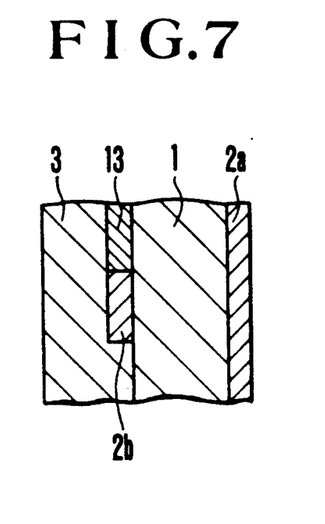
FIGS. 7 and 8 are partial cross sectional views of other embodiments of gas sensors of the invention, respectively.
Figure 8:
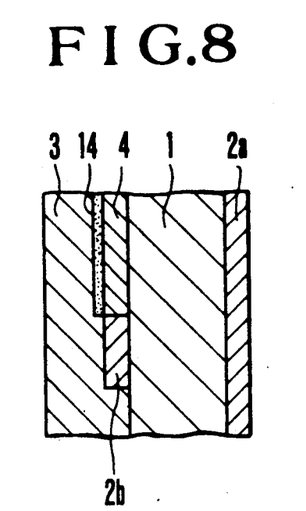

FIGS. 7 and 8 are cross sectional views of the main sections showing methods of losing the catalyst function of the lead electrode according to further other embodiments of the invention. In the diagram, the parts and components as those shown in FIG. 5 are designated by the same reference numerals and their descriptions are omitted.

In FIG. 7, a thin film is formed onto the surface of a platinum lead electrode by using a metal material which does not have the electrode reaction by using a method such as metal plating, vacuum evaporation deposition, sputtering, metal paste coating, or the like. Thereafter, the thin film is sintered to thereby form an alloy layer 13. In the alloy layer 13 serving as a lead electrode, since an alloy of platinum and a metal having no electrode reaction is formed, the capability to ionize oxygen is lost. Thus, the lead electrode portion loses the catalyst performance and has only the conductivity.

The method of the embodiment of FIG. 7 will be further practically explained. First, a dirt on the surface of the lead electrode is removed by using acetone or the like. The sputtering of gold is executed for ten minutes and the fused gold particles are deposited onto the lead electrode surface, thereby forming a thin film. Thereafter, the sintering is performed for one hour at 1050° C. in the atmosphere by using the electric furnace and the gas diffusion layer 3 is formed on the outside of the device by using the flame coating. The limiting current value is measured. Thus, the pump current was saturated to a predetermined value as shown in (a) in FIG. 3.

In FIG. 8, a thin film 14 is formed onto the lead electrode 4 by using a ceramics material or the like by a method of vacuum evaporation deposition or sputtering. Zirconia is most preferable as a ceramics material. This is because zirconia is used for the solid state electrolyte 1, a coefficient of thermal expansion of zirconia of the electrolyte 1 is the same as that of zirconia of the thin film 14 and they are hardly influenced by the thermal distortion due to the heat treatment or the like. On the other hand, since the thin film 14 is formed thinner as compared with the conventional glass insulative layer, the influence is small even in the case of forming the gas diffusion layer 3 in the next step. Moreover, since the lead electrode 4 and exhaust gas are completely isolated, there is no influence by the erroneous current upon measurement of the A/F.

A whole construction of the air-fuel ratio measuring gas sensor using the ultra fine particulates will now be described with reference to FIG. 9.

Figure 9:
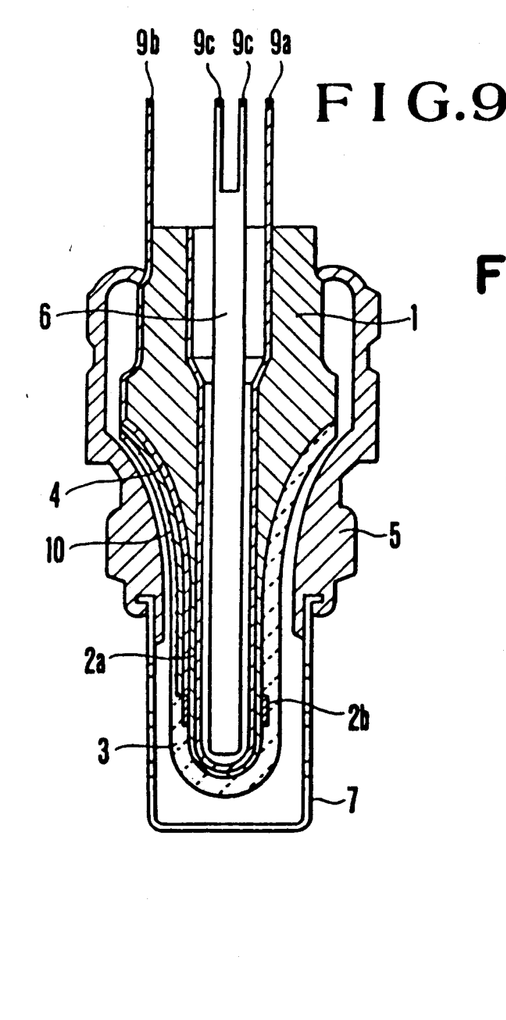
FIG. 9 is a whole cross sectional view showing an assembly state of the gas sensor of the invention.

In FIG. 9, the solid state electrolyte 1 is fixed to a cap member 5. An outer cylinder 7 to protect the gas diffusion layer 3 from impurities in the exhaust gas is attached to the tip of the cap member 5. The heater 6 to heat the device to temperatures within a range from 600° to 700° C. and to convert zirconia as a device material into the electrolyte is also provided in the solid state electrolyte 1. Further, the ultra fine particulate layer 10 is formed on the lead electrode 4 by the foregoing method.

On the other hand, as shown in FIG. 9, lead wires 9a, 9b, and 9c to extract electric signals and to apply voltages are connected to the inside reactive electrode 2a, outside reactive electrode 2b, and heater 6, respectively.

The air-fuel ratio measuring gas sensor manufactured as mentioned above is attached to an exhaust pipe of an automobile. The heater 6 is energized to heat the solid state electrolyte 1 of the device main body to a temperature of about 700° C. A voltage is applied to the device. In this case, since the influence by the erroneous current as in the conventional sensor is not exerted, the concentration of oxygen or unburnt gas can be accurately detected. Thus, the air-fuel ratio of the air-fuel mixture can be correctly detected.

Figures 10A, 10B, 10C, 10D:
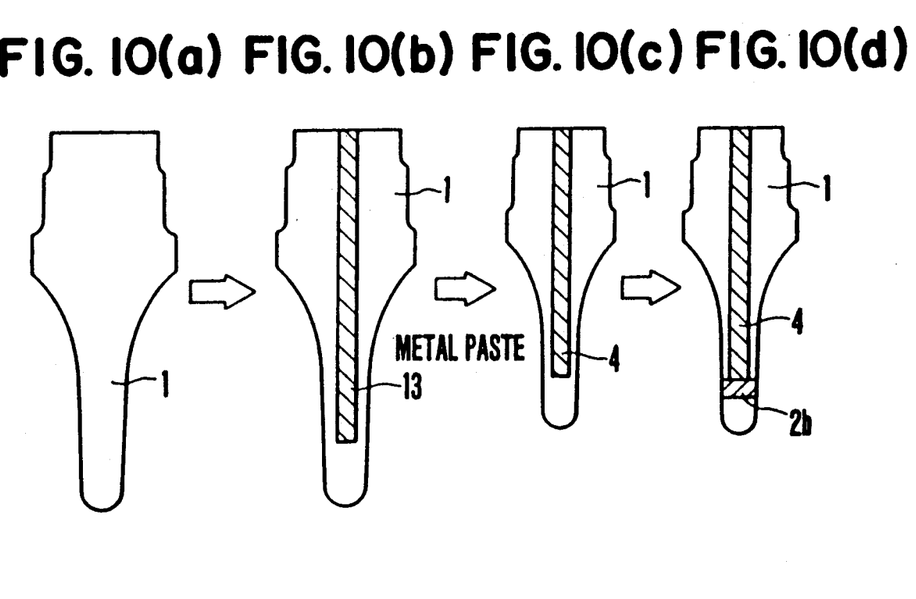

FIG. 10 shows another embodiment of a method of manufacturing an air-fuel ratio measuring gas sensor of the invention. The method of the embodiment is fundamentally similar to the embodiment shown in FIG. 5 in which the lead electrode surface is fused by the high temperature heat source and the catalyst function is lost. However, in the embodiment of FIG. 10, the high temperature heat source is not separately provided but when the solid state electrolyte 1 is sintered, the lead electrode is simultaneously fused.

In FIG. 10, (a) shows an external view of the solid state electrolyte 1 which was green molded by using the die. As shown in (b), the metal paste 13 is coated onto the mold and, thereafter, the mold is sintered at a high temperature. It is preferable to use a metal paste having no catalyst function. Thus, since the solid state electrolyte 1 is sintered at a high temperature, it is contracted by about 25% as shown in (c) in FIG. 10. In association with the high temperature sintering, the metal paste 13 coated is fused and adhered onto the electrolyte 1. Thereafter, the outside reactive electrode 2b is formed like an annular strip as shown in (d) in FIG. 7 and the inside reactive electrode is formed onto the whole surface of the inside by the platinum plating in the next step. As the metal paste, it is desirable to use a material such that after completion of the high temperature sintering, the resistance value across the lead electrode is 2 ohms or less in consideration of the problems of the reactivity and the like. It is preferable to form the metal paste like a thin film. This is because the gas diffusion layer is formed on the outside of the metal paste and by forming the lead electrode in a thin film shape, the influence on the gas diffusion layer is reduced and the thinner film gas diffusion layer can be easily formed.

The lead electrode forming method using the metal paste in the embodiment of FIG. 10 will now be further practically explained.

First, a silver-palladium paste is coated onto the green molded solid state electrolyte 1 by a brush coating method and a lead electrode is formed. Thereafter, they are naturally dried for two hours and are thermally treated in the electric furnace at 1500° C. for one hour in the atmosphere. Thus, the lead electrode having a film thickness of 37 μm in which a resistance value across the lead electrode is 0.4 ohm is formed. In the next step, the outside reactive electrode is formed by the platinum plating so as to come into contact with the lead electrode. The gas diffusion layer is formed on the outside of the outside reactive electrode. The current-voltage characteristic is measured. Thus, the same characteristic as that shown in (a) in FIG. 3 was obtained.

Figure 11:
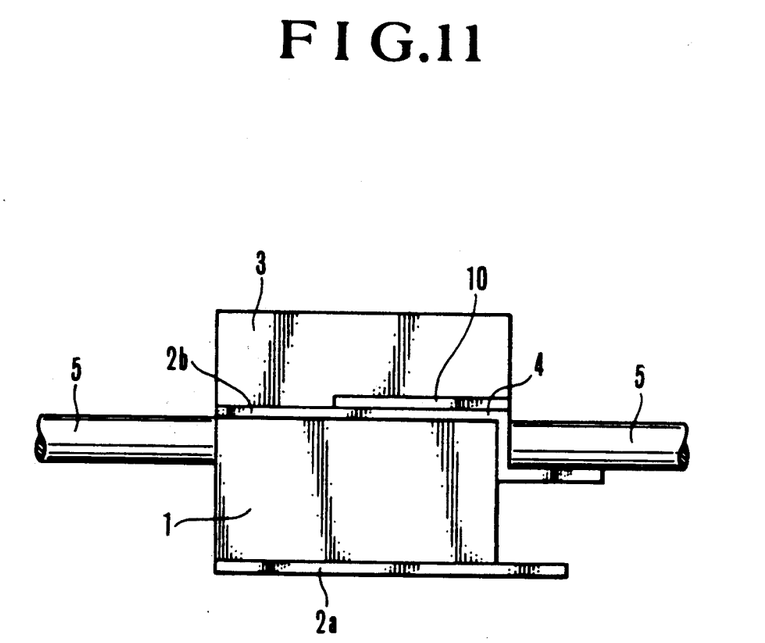
FIG. 11 is a cross sectional view showing another embodiment of the gas sensor according to the present invention.

FIG. 11 shows still another embodiment of an air-fuel ratio measuring gas sensor of the invention.

The embodiment relates to an example in which it is applied to the air-fuel ratio measuring gas sensors of not only the foregoing test tube type structure but also a laminate type structure.

In FIG. 11, a method of manufacturing the gas sensor of the laminate type structure will now be described. First, the solid state electrolyte 1 is molded like a flat plate shape and sintered. Thereafter, platinum is plated onto both sides of the electrolyte 1. Next, the thin film layer 10 of the ultra fine particulate sintered material is formed onto the lead electrode 4 other than the outside reactive electrode 2b. The gas diffusion layer is formed on the layer 10.

Hitherto, the lead electrodes have been separately formed at different positions on both sides of the solid state electrolyte. However, by applying the invention to the laminate type structure, the lead electrodes can be formed in accordance with the widths of the reactive electrodes. There is an advantage such that the sensor can be miniaturized.

We claim:

1. A gas sensor for measuring an air-fuel ratio comprising:
   a sold state electrolyte layer made of an oxygen ion conductive metal oxide, having first and second surfaces;
   a first electrode of a porous thin film having a catalyst function which is coated on the first surface of said solid state electrolyte layer;
   a second electrode of a porous thin film having the catalyst function which is coated on the second surface of the solid state electrolyte layer;
   a catalyst inactive region formed by fusing a portion of the second electrode other than a region of a predetermined area of the second electrode; and
   a gas diffusion layer which covers at least the region of the predetermined area of the second electrode and is made of a porous electric insulative metal oxide.

2. A method of manufacturing a gas sensor for measuring an air-fuel ratio, comprising the steps of:
   injecting an oxygen ion conductive metal oxide material into a predetermined die and molding so as to form a metal oxide mold;
   sintering said metal oxide mold so as to form a solid state electrolyte layer having first and second surfaces;
   forming first and second porous thin film electrodes each having a catalyst function onto the first and second surfaces, respectively, of said solid state electrolyte layer;
   thermally treating a portion of a surface of the second electrode, other than a reactive electrode region of predetermined area, and fusing, thereby destroying the catalyst function of the thermally treated and fused portion of the second electrode; and
   coating a porous electric insulative metal oxide onto the reactive electrode region of a predetermined area and sintering, thereby forming a gas diffusion layer.

3. A method according to claim 2, wherein said thermally treating and fusing includes a step of striking a plasma stream from a plasma jet torch onto the second electrode surface other than said reactive electrode region.

4. A method according to claim 2, wherein said thermally treating and fusing includes a step of striking a laser beam from a laser apparatus onto the second electrode surface other than said reactive electrode region.

5. A method according to claim 2, wherein said thermally treating and fusing includes a step of striking an electron beam from an electron beam generating apparatus onto the second electrode surface other than said reactive electrode region.

6. A method of manufacturing a gas sensor for measuring an air-fuel ratio, comprising the steps of:
   injecting an oxygen ion conductive metal oxide material into a predetermined die and molding so as to form a metal oxide mold;
   forming a lead electrode onto a second surface of said metal oxide mold;
   sintering said metal oxide mold so as to form a solid state electrolyte layer and fusing the lead electrode so as to destroy a catalyst function of the lead electrode;
   forming a porous thin film electrode connected to said lead electrode and having a catalyst function onto the second surface of said solid state electrolyte layer, while forming a first thin film electrode having a catalyst function, on a first surface of said solid state electrolyte layer; and
   coating a porous electric insulative metal oxide onto a surface of at least said porous thin film electrode connected to said lead electrode and sintering, thereby forming a gas diffusion layer.

7. A method according to claim 6, wherein said step of forming said lead thin film electrode includes a step of coating a silver-palladium paste onto one surface of said metal oxide mold by using a brush.

8. A method according to claim 6, wherein said sintering is carried out after forming the lead electrode.

9. A method according to claim 8, wherein the sintering the metal oxide mold is performed simultaneously with said fusing the lead electrode.

10. A gas sensor for measuring an air-fuel ratio comprising:
    a solid state electrolyte layer made of an oxygen ion conductive metal oxide, and having first and second surfaces;
    a first electrode of a porous thin film having a catalyst function which is coated on the first surface of said solid state electrolyte layer;
    a second electrode of a porous thin film having the catalyst function which is coated on the second surface of said solid state electrolyte layer;
    a catalyst inactive region formed of a sintered alloy layer of material of ultra fine particulate and material of said second electrode which is formed at an interface with the second electrode so that the catalyst function of a portion of the second electrode, other than a region of a predetermined area of the second electrode, is prevented; and
    a gas diffusion layer which covers at least the region of the predetermined area of the second electrode.

11. A sensor according to claim 10, wherein the material of the ultra fine particulate is a material selected from the group consisting of titanium, tin, silicon, nickel, and gold.

12. A gas sensor for measuring an air-fuel ratio comprising:
    a solid state electrolyte layer made of an oxygen ion conductive metal oxide, and having first and second surfaces;
    a first electrode of a porous thin film having a catalyst function which is coated on the first surface of said solid state electrolyte layer;
    a second electrode of a porous thin film having the catalyst function which is coated on the second surface of said solid state electrolyte layer;
    an electrode shielding layer, which is non-catalytic, and which covers a surface of the second electrode other than a region of a predetermined area of said second electrode, said electrode shielding layer being made of a sintered material of ultra fine particulate so as to isolate the surface of the second electrode other than the region of the predetermined area of the second electrode, so that the catalyst function of the second electrode, other than the region of the predetermined area of the second electrode, is prevented, said electrode shielding layer including a fused film of said ultra fine particulate formed on the surface of said second electrode; and
    a gas diffusion layer which covers at least the region of the predetermined area of the second electrode.

13. A sensor according to claim 12, wherein said fused film is a dense film through which hydrogen molecules cannot pass.

14. A sensor according to claim 13, wherein the material of the ultra fine particulate is a material selected from the group consisting of titanium, tin, silicon, nickel, and gold.

15. A sensor according to claim 12, wherein the material of the ultra fine particulate is a material selected from the group consisting of titanium, tin, silicon, nickel, and gold.

16. A sensor according to claim 12, wherein the electrode shielding layer is a layer which blocks contact of gas molecules with a three-phase interface.

17. A gas sensor for measuring an air-fuel ratio comprising:
    a solid state electrolyte layer made of an oxygen ion conductive metal oxide, and having first and second surfaces;
    a first electrode of a porous thin film having a catalyst function which is coated on the first surface of said solid state electrolyte layer;
    a second electrode of a porous thin film having the catalyst function which is coated on the second surface of said solid state electrolyte layer;
    an electrode shielding layer, which is non-catalytic, and which covers a surface of the second electrode other than a region of a predetermined area of said second electrode, said electrode shielding layer being made of a sintered material of ultra fine particulate so as to isolate the surface of the second electrode other than the region of the predetermined area of the second electrode, so that the catalyst function of the second electrode, other than the region of the predetermined area of the second electrode, is prevented, the sintered material being selected from the group consisting of titanium, tin, silicon, nickel and gold; and
    a gas diffusion layer which covers at least the region of the predetermined area of the second electrode.

18. A sensor according to claim 17, wherein the first and second surfaces are, respectively, inner and outer surfaces, with the first electrode coated on the inner surface and the second electrode coated on the outer surface.

19. A gas sensor for measuring an air-fuel ratio comprising:
a solid state electrolyte layer made of an oxygen ion conductive metal oxide, and having first and second surfaces;
a first electrode of a porous thin film having a catalyst function which is coated on the first surface of said solid state electrolyte layer;
a second electrode of a porous thin film having the catalyst function which is coated on the second surface of said solid state electrolyte layer;
an electrode shielding layer, which is non-catalytic, and which covers a surface of the second electrode other than a region of a predetermined area of said second electrode, said electrode shielding layer being made of a sintered material of ultra fine particulate so as to isolate the surface of the second electrode other than the region of the predetermined area of the second electrode, so that the catalyst function of the second electrode, other than the region of the predetermined area of the second electrode, is prevented, the material of ultra fine particulate being a ceramic material; and
a gas diffusion layer which covers at least the region of the predetermined area of the second electrode.

20. A sensor according to claim 19, wherein said ceramics material is zirconia.

21. A sensor according to claim 19, wherein said ceramics material is a fused film, the fused film being sufficiently dense such that hydrogen molecules cannot pass therethrough.

22. A method of manufacturing a gas sensor for measuring an air-fuel ratio, comprising the steps of:
injecting an oxygen ion conductive metal oxide material into a predetermined die and molding to form a metal oxide mold;
sintering said metal oxide mold so as to form a solid state electrolyte layer;
forming first and second porous thin film electrodes each having a catalyst function onto first and second surfaces, respectively, of said solid state electrolyte layer;
forming, by coating, an ultra fine particulate layer onto a portion of a surface of the second porous thin film electrode other than a reactive electrode region of a predetermined area on said second porous thin film electrode, said ultra fine particulate layer being made of metal ultra fine particulates having no catalyst function, with ultra fine particulates of the ultra fine particulate layer being such that, after sintering, the portion of the surface of the second porous thin film electrode other than the reactive electrode region is isolated, so that the catalyst function of the second porous thin film electrode, other than the reactive electrode region of the predetermined area on the second porous thin film electrode, is prevented, the forming said ultra fine particulate layer including a step of plating the metal ultra fine particulates onto the portion of the second electrode surface other than said reactive electrode region;
sintering said coated ultra fine particulate layer so as to form a non-catalytic shield layer; and
coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

23. A method of manufacturing a gas sensor for measuring an air-fuel ratio, comprising the steps of:
injecting an oxygen ion conductive metal oxide material into a predetermined die and molding to form a metal oxide mold;
sintering said metal oxide mold so as to form a solid state electrolyte layer;
forming first and second porous thin film electrodes each having a catalyst function onto first and second surfaces, respectively, of said solid state electrolyte layer;
forming, by coating, an ultra fine particulate layer onto a portion of a surface of the second porous thin film electrode other than a reactive electrode region of a predetermined area on said second porous thin film electrode, said ultra fine particulate layer being made of metal ultra fine particulates having no catalyst function, with ultra fine particulates of the ultra fine particulate layer being such that, after sintering, the portion of the surface of the second porous thin film electrode other than the reactive electrode region is isolated, so that the catalyst function of the second porous thin film electrode, other than the reactive electrode region of the predetermined area on the second porous thin film electrode, is prevented, the forming the ultra fine particulate layer including a step of vacuum evaporation depositing the metal ultra fine particulates onto the portion of the second electrode surface other than said reactive electrode region;
sintering said coated ultra fine particulate layer so as to form a non-catalytic shield layer; and
coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

24. A method of manufacturing a gas sensor for measuring an air-fuel ratio, comprising the steps of:
injecting an oxygen ion conductive metal oxide material into a predetermined die and molding to form a metal oxide mold;
sintering said metal oxide mold so as to form a solid state electrolyte layer;
forming first and second porous thin film electrodes each having a catalyst function onto first and second surfaces, respectively, of said solid state electrolyte layer;
forming, by coating, an ultra fine particulate layer onto a portion of a surface of the second porous thin film electrode other than a reactive electrode region of a predetermined area on said second porous thin film electrode, the ultra fine particulate layer being made of metal ultra fine particulates having no catalyst function, with ultra fine particulates of the ultra fine particulate layer being such that, after sintering, the portions of the surface of the second porous thin film electrode other than the reactive electrode region is isolated, so that the catalyst function of the second porous thin film electrode, other than the reactive electrode region of the predetermined area on the second porous thin film electrode, is prevented, the step of forming the ultra fine particulate layer including a step of forming a thin film of said metal ultra fine particulates onto the portion of the second electrode surface other than said reactive electrode region by sputtering;

sintering said coated ultra fine particulate layer so as to form a non-catalytic shield layer; and coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

25. A method of manufacturing a gas sensor for measuring an air-fuel ratio, comprising the steps of:

injecting an oxygen ion conductive metal oxide material into a predetermined die and molding to form a metal oxide mold;

sintering said metal oxide mold so as to form a solid state electrolyte layer;

forming first and second porous thin film electrodes each having a catalyst function onto first and second surfaces, respectively, of said solid state electrolyte layer;

forming, by coating, an ultra fine particulate layer onto a portion of a surface of the second porous thin film electrode other than a reactive electrode region of a predetermined area on said second porous thin film electrode, the ultra fine particulate layer being made of metal ultra fine particulates having no catalyst function, with ultra fine particulates of the ultra fine particulate layer being such that, after sintering, the portion of the surface of the second porous thin film electrode other than the reactive electrode region is isolated, so that the catalyst function of the second porous thin film electrode, other than the reactive electrode region of the predetermined area on the second porous thin film electrode, is prevented, the step of forming the ultra fine particulate layer including a step of coating a metal paste of said metal ultra fine particulates onto the portion of the second electrode surface other than said reactive electrode region and forming a thin film;

sintering said coated ultra fine particulate layer so as to form a non-catalytic shield layer; and coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

26. A method according to claim 25, wherein said metal ultra fine particulates are nickel whose average grain diameter is 0.04 μm, and the steps of forming and sintering said ultra fine particulate layer includes steps of producing a diffusion liquid of a ratio of ethyl alcohol of 20 cc for nickel ultra fine particulates of 5 g, coating said diffusion liquid onto the portion of the second electrode surface other than said reactive electrode region, drying said coated film, and thereafter sintering the dried film at 950° C. for one hour in an argon atmosphere.

27. A method of manufacturing a gas sensor for measuring an air-fuel ratio, comprising the steps of:

injecting an oxygen ion conductive metal oxide material into a predetermined die and molding to form a metal oxide mold;

sintering said metal oxide mold so as to form a solid state electrolyte layer;

forming first and second porous thin film electrodes each having a catalyst function onto first and second surfaces, respectively, of said solid state electrolyte layer;

forming, by coating, an ultra fine particulate layer onto a portion of a surface of the second porous thin film electrode other than a reactive electrode region of a predetermined area on said second porous thin film electrode, said ultra fine particulate layer being made of ceramics ultra fine particulates having no catalyst function, with ultra fine particulates of the ultra fine particulate layer being such that, after sintering, the portion of the surface of the second porous thin film electrode other than the reactive electrode region is isolated, so that the catalyst function of the second porous thin film electrode, other than the reactive electrode region of the predetermined area on the second porous thin film electrode, is prevented, the step of forming the ultra fine particulate layer including a step of vacuum evaporation depositing said ceramics ultra fine particulates onto the portion of the second electrode surface other than said reactive electrode region;

sintering said coated ultra fine particulate layer so as to form a non-catalytic shield layer; and coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

28. A method of manufacturing a gas sensor for measuring an air-fuel ratio, comprising the steps of:

injecting an oxygen ion conductive metal oxide material into a predetermined die and molding to form a metal oxide mold;

sintering said metal oxide mold so as to form a solid state electrolyte layer;

forming first and second porous thin film electrodes each having a catalyst function onto first and second surfaces, respectively, of said solid state electrolyte layer;

forming, by coating, an ultra fine particulate layer onto a portion of a surface of the second porous thin film electrode other than a reactive electrode region of a predetermined area on said second porous thin film electrode, the ultra fine particulate layer being made of ceramics ultra fine particulates having no catalyst function, with ultra fine particulates of the ultra fine particulate layer being such that, after sintering, the portion of the surface of the second porous thin film electrode other than the reactive electrode region is isolated, so that the catalyst function of the second porous thin film electrode, other than the reactive electrode region of the predetermined area on the second porous thin film electrode, is prevented, the step of forming the ultra fine particulate layer including a step of coating said ceramics ultra fine particulates onto the portion of the second electrode surface other than said reactive electrode by sputtering;

sintering said coated ultra fine particulate layer so as to form a non-catalyst shield layer; and coating a porous electric insulative metal oxide onto the reactive electrode region of the predetermined area of said second porous thin film electrode formed on said second surface of the solid state electrolyte layer and sintering said insulative metal oxide, thereby forming a gas diffusion layer.

29. A method of manufacturing a gas sensor for measuring an air-fuel ratio, comprising the steps of:

injecting an oxygen ion conductive metal oxide material into a predetermined die and molding so as to form a metal oxide mold;

sintering said metal oxide mold so as to form a solid state electrolyte layer having first and second surfaces;

forming first and second porous thin film electrodes each having a catalyst function onto the first and second surfaces, respectively, of said solid state electrolyte layer;

forming, by coating, an ultra fine particulate layer on a portion of a surface of the second electrode, other than a reactive electrode region of a predetermined area, and forming an alloy layer of material of the ultra fine particulate layer and material of the second electrode such that thereby the catalyst function of the second electrode, other than of the reactive electrode region of the predetermined area, is lost; and coating a porous electric insulative metal oxide onto the reactive electrode region of a predetermined area and sintering, thereby forming a gas diffusion layer.

* * * * *